United States Patent [19]

Arcari et al.

[11] 3,972,883

[45] Aug. 3, 1976

[54] 1,6-DIMETHYL-8β-[2' OR 3'-PYRROYLOXYETHYL OR SUBSTITUTED PYRROYLOXYETHYL]-10α-METHOXYERGOLENE COMPOUNDS

[75] Inventors: Giuliana Arcari; Luigi Bernardi, both of Milan; Germano Bosisio, Palazzolo Milanese; Alfredo Glässer; Innocenzio Sinatra, both of Milan, all of Italy

[73] Assignee: Societa Farmaceutici Italia S.p.A., Milan, Italy

[22] Filed: Jan. 28, 1974

[21] Appl. No.: 436,927

[30] Foreign Application Priority Data

Feb. 2, 1973  Italy................................. 19941/73

[52] U.S. Cl............................. 260/285.5; 424/261
[51] Int. Cl.²....................................... C09D 457/02
[58] Field of Search.................................. 260/285.5

[56] References Cited
UNITED STATES PATENTS

| | | | |
|---|---|---|---|
| 3,228,943 | 1/1966 | Bernardi et al. | 260/285.5 |
| 3,585,201 | 6/1971 | Arcamone et al. | 260/285.5 |
| 3,732,231 | 5/1973 | Semonsky et al. | 260/285.5 |

FOREIGN PATENTS OR APPLICATIONS

| | | | |
|---|---|---|---|
| 7,102,982 | 9/1971 | Netherlands | 260/285.5 |
| 1,230,260 | 4/1971 | United Kingdom | 260/285.5 |

OTHER PUBLICATIONS

Beran et al., Coll. Czech. Chem. Commun. vol. 34, pp. 2819–2823, 1969.
Bernardi et al., Chem. Abstr. vol. 62, col. 4069–4070h, 1965.
Beran et al., Chem. Abstr. vol. 71, 91725v, 1969.

*Primary Examiner*—Alton D. Rollins
*Assistant Examiner*—Mary C. Vaughn
*Attorney, Agent, or Firm*—Stevens, Davis, Miller & Mosher

[57] ABSTRACT

Ergoline derivatives are disclosed having the general formula

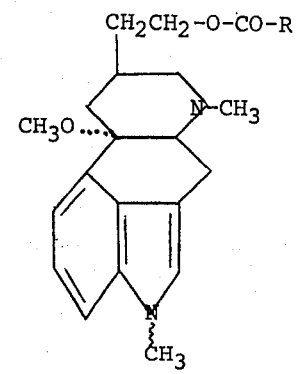

wherein R is selected from the group consisting of a lower alkyl radical having from 1 to 4 carbon atoms; an —NH-lower alkyl radical having from 1 to 4 carbon atoms; a free or substituted phenyl- or 2-furanoyl radical; the —O—CH$_2$—C$_6$H$_5$ radical; a (3)- or (4)-pyridine radical free or substituted by a methyl radical or a chlorine or bromine atom; a pyrrole radical of formula

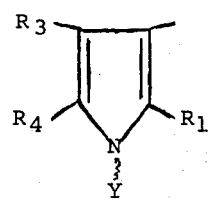 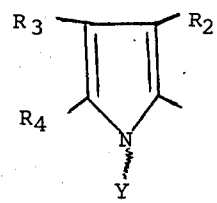

wherein
Y is hydrogen, a lower alkyl radical having from 1 to 4 carbon atoms or phenyl;
R$_1$ is hydrogen or methyl;
R$_2$ is hydrogen, methyl or halogen; and
R$_3$ and R$_4$ are the same or different and are hydrogen, halogen, a lower alkyl radical having from 1 to 4 carbon atoms, carbethoxy, or a lower alkyloxy radical having from 1 to 4 carbon atoms.

Novel processes for the preparation of these compounds are also disclosed.

6 Claims, No Drawings

1,6-DIMETHYL-8β-[2' OR 3'-PYRROYLOXYETHYL OR SUBSTITUTED PYRROYLOXYETHYL]-10α-METHOXYERGOLINE COMPOUNDS

The present invention relates to new ergoline derivatives and to novel processes for their preparation.

More particularly, the present invention relates to new esters of 1,6-dimethyl-10α-methoxy-8-hydroxyethylergoline having the general formula:

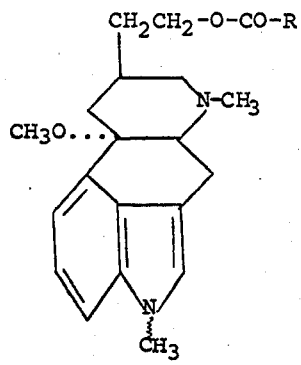

VII wherein R is selected from the group consisting of a lower alkyl radical having from 1 to 4 carbon atoms; an —NH-lower alkyl radical having from 1 to 4 carbon atoms; a free or substituted phenyl- or 2-furanoyl radical; the —O—CH$_2$—C$_6$H$_5$ radical; a (3)- or (4)-pyridine radical free or substituted by a methyl radical or a chlorine or bromine atom; a pyrrole radical of formula

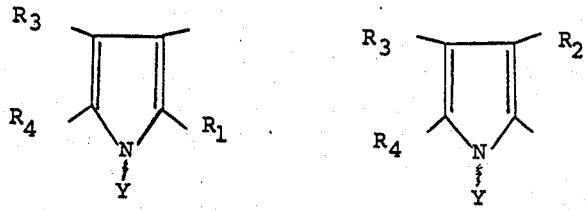

wherein
Y is hydrogen, a lower alkyl radical having from 1 to 4 carbon atoms or phenyl;
R$_1$ is hydrogen or methyl;
R$_2$ is hydrogen, methyl or halogen; and
R$_3$ and R$_4$ are the same or different and are hydrogen, halogen, a lower alkyl radical having from 1 to 4 carbon atoms, carbethoxy, or a lower alkyloxy radical having from 1 to 4 carbon atoms.

The invention also includes novel processes for the preparation of these compounds.

The new esters of 8-hydroxyethylergoline possess a remarkable adrenolytic and antiserotoninic activity.

They have been prepared according to the following scheme:

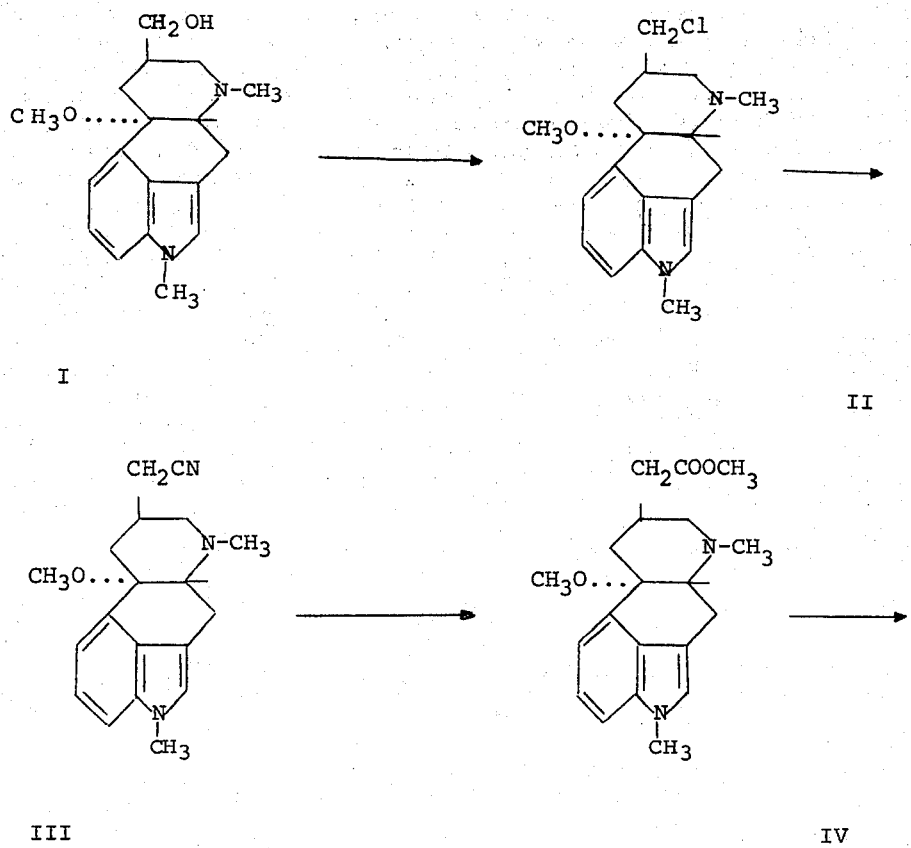

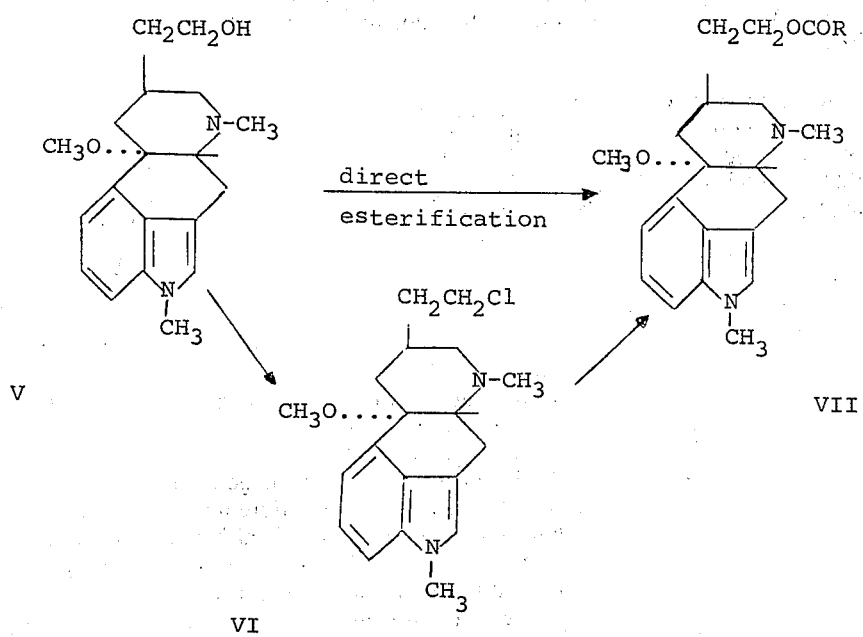

The starting material for preparing compounds of the present invention is, preferably, 1-methyl-lumilysergol-10-methylether or 1,6-dimethyl-8β-hydroxymethyl-10α-methoxyergoline (I), described and claimed in the Bernardi et al. U.S. Pat. No. 3,228,943. It is reacted at a temperature between 40° and 50° C with the chloride of an aryl- or alkylsulphonic-acid, such as tosyl chloride or mesyl chloride, in pyridine and in the presence of pyridinium chloride, to give the corresponding 8-chloromethyl derivative. This compound, that is, 1,6-dimethyl-8β-chloromethyl-10α-methoxyergoline (II), is treated with an alkaline cyanide, such as sodium or potassium cyanide in a suitable solvent, such as dimethylsulphoxide, at the temperature of 100°–120° C for a period between 4 and 8 hours. The product thus formed, that is, 1,6-dimethyl-8β-cyanomethyl-10α-methoxyergoline (III), is isolated and characterized: it has never been described in the previous literature. This product is subjected to alkaline hydrolysis, preferably with potassium hydroxide in water/ethanol/dioxan solution, under reflux conditions for a few hours.

The corresponding acid is not isolated, but is transformed into its methyl ester by the action of methanol and sulfuric acid at room temperature for 24 hours. After pouring the reaction mixture onto ice, the product is made alkaline with ammonia and extracted with a solvent immiscible with water, such as chloroform. The compound obtained, that is 1,6-dimethyl-10α-methoxy-8β-ergolinylacetic acid (IV) methylester, never described in the literature, is dissolved in anhydrous tetrahydrofuran and treated with a suitable reducing agent such as lithium and aluminum hydride, operating at 40°–70° C for some hours. At the end of the reaction, the whole is cooled at 0° C, combined cautiously with water to remove the excess of LiAlH$_4$, filtered off and concentrated under vacuum to dryness.

The residue is taken up with acetone and filtered. There is obtained the new compound 1,6-dimethyl-8β-hydroxyethyl-10α-methoxyergoline (V). By esterification of (V) with a suitable acylating agent, the corresponding esters (VII) are obtained. The acylating agents may be selected from among the most widely different ones and generally from the group consisting of a lower aliphatic acid containing from 1 to 4 carbon atoms, a carbonic or carbamic acid derivative, free or substituted benzoic and furan-2-carboxylic acids, nicotinic and isonicotinic acid free or substituted with a methyl, chloro or bromo, a pyrrol-2- or pyrrol-3-carboxylic acid of structure:

wherein Y, $R_1$, $R_2$, $R_3$, $R_4$ have the above meanings.

In the case of aliphatic acids, of carbonic and carbamic acid derivatives, of nicotinic and isonicotinic acids, the esterification can be performed in per se known manner, by the reaction of 1,6-dimethyl-8β-hydroxyethyl-10α-methoxyergoline (V) with a suitable derivative of the desired acid such as the chloride or anhydride, either in the presence or absence of a base, whereupon the desired ester is isolated and purified in per se known manner.

In the case of acids containing the furanic or pyrrolic ring, since these are particularly unstable with respect to the usual chlorinating agents (phosphorus oxychloride, phosphorus pentachloride and thionyl chloride), it is better first to convert the hydroxyethylergoline (V) into 1,6-dimethyl-8β-chloroethyl-10α-methoxyergoline (VI) by reaction with the chloride of an aryl- or alkylsulphonic-acid in the presence of pyridinium chloride, under conditions analogous to those previously described (I → II). The intermediate thus obtained, isolated and characterized, has never been described before in the literature. It is reacted with a salt of the desired acid, in an aprotic polar solvent such as dimethylsulphoxide, at a temperature between 40° and 150° C, over a period of time varying from 3 to 10 hours. At the end of the reaction, the compound is cooled, the mixture is diluted with water, and the crude product is filtered off. Later it is purified according to the usual methods, for example by crystallisation or by column chromatography. The compounds of the present invention may be readily transformed into their addition salts with a pharmaceutically acceptable acid, such as maleic or tartaric acid, according to the usual methods for this type of compounds.

The intermediates (IV) and (V), having a slight pharmacological activity, can also be prepared according to the following alternative reactions.

The N-methyl-lysergic acid is transformed into the corresponding chloride which, by means of the well known Arndt-Eistert reaction (e.g., see The Merck Index, Eighth (1968) Edition, p. 1140), yields the methyl ester of 1,6-dimethyl-Δ⁹-ergolenil-8-acetic acid. This is dissolved in methanol and sulphuric acid and, by irradiation with light of suitable wave length, gives the desired compounds (IV). For the intermediate (V), the 6-methyl-8β-hydroxyethyl-Δ⁹-ergolene, dissolved in liquid ammonia, is reacted with methyl iodide in the presence of potassium amide to give 1,6-dimethyl-8β-hydroxyethyl-Δ⁹-ergolene, that in methanol and sulphuric acid, by irradiation with light of suitable wave length, gives the desired compound.

Here and elsewhere in the description where reference is made to irradiation with light of suitable wave length, irradiation with light from a 250 watt Philip/HPLR lamp may be mentioned by way of example.

The adrenolytic activity of the new esters has been studied in comparison with that of Nicergoline [1,6-dimethyl-8β-(5′-bromonicotinoyloxymethyl)-10α-methoxyergoline] and of dihydroergotamine. The activity "in vitro" has been determined employing seminal small bladder of Guinea-pig immersed in Tyrode liquid wherein oxygen and 5% carbon dioxide are bubbled.

The bath temperature is maintained constant at 38°C. The contractions induced by Adrenaline are registered on a chimograph by means of an isotonic lever. The activity of the drug under examination is expressed as the concentration in mcg/ml able, after 3 minutes of contact, to inhibit 50% of the contractions caused by 1 mcg/ml of Adrenaline ($IC_{50}$).

TABLE I

| SUBSTANCE | Adrenolytic activity "in vitro" $IC_{50}$ (mcg/ml) |
|---|---|
| 1,6-Dimethyl-8β-[2′-pyrroyloxyethyl]-10α-methoxyergoline | 0.005 |
| 1,6-Dimethyl-8β-[2′-methyl-3′-pyrroyloxyethyl]-10α-methoxyergoline | 0.001 |
| 1,6-Dimethyl-8β-[3′,5′-dimethyl-2′-pyrroyloxyethyl]-10α-methoxyergoline | 0.05 |
| 1,6-Dimethyl-8β-[1′,3′,5′-trimethyl-2′pyrroyloxyethyl]-10α-methoxyergoline | 0.1 |
| 1,6-Dimethyl-8β-[1′-ethyl-2′-pyrroyloxyethyl]-10α-methoxyergoline | 0.001 |
| Nicergoline | 0.001 |
| Dihydroergotamine | 0.015 |

For the adrenolytic activity "in vivo" the method of Luduena et al. (Arch. int. Pharmacodyn., 122, 11 1959) has been used, based on the evaluation of the protective action of the adrenolytic compounds against the lethal effects of Adrenaline.

The drugs under examination are administered by the endovenous route dissolved in water, and by the oral route they are dissolved or suspended in 5% arabic gum, respectively at 5 and 60 minutes before a fixed dose of 200 mcg/Kg of Adrenaline by the endovenous route.

Always 10 rats have been employed per group.

The activity of the drug is expressed as the dose protecting 50% of the animals from the lethal effects of Adrenaline administered by the endovenous route ($ED_{50}$).

TABLE II

| SUBSTANCE | Adrenolitic activity "in vivo" $ID_{50}$ mg/kg os | $\frac{LD_{50}}{ID_{50}}$ os |
|---|---|---|
| 1,6-Dimethyl-8β-[2′-pyrroyloxyethyl]-10α-methoxyergoline | 0.06 | 6600 |
| 1,6-Dimethyl-8β-[2′-methyl-3′-pyrroyloxyethyl-10α-methoxyergoline | 0.1 | 1300 |
| 1,6-Dimethyl-8β-[3′,5′-dimethyl-2′-pyrroyloxyethyl]-10α-methoxyergoline | 0.12 | 3750 |
| 1,6-Dimethyl-8β-[1′,3′,5′-trimethyl-2′-pyrroyloxyethyl]-10α-methoxyergoline | 0.1 | 1300 |
| 1,6-Dimethyl-8β-[1′-ethyl-2′-pyrroyloxyethyl]-10α-methoxyergoline | 0.025 | 5200 |
| Nicergoline | 7 | 90 |
| Dihydroergotamine | 15 | — |

In order to evaluate the toxicity of the drugs under examination, increasing doses are administered to groups of 5–10 mice which are then followed for a period of 7 days.

For administration by the oral route, the compounds are dissolved or suspended, according to the solubility, in 5% arabic gum. The $LD_{50}$ expresses the dose of drug which causes the death of 50% of the animals.

TABLE III

| SUBSTANCE | $LD_{50}$ mg/kg os |
|---|---|
| 1,6-Dimethyl-8β-[2′-pyrroyloxyethyl]-10α-methoxyergoline | 450 |
| 1,6-Dimethyl-8β-[2′-methyl-3′-pyrroyloxyethyl]- | |

| | |
|---|---|
| 10α-methoxyergoline | 100 |
| 1,6-Dimethyl-8β-[3',5'-dimethyl-2'-pyrroyl-oxyethyl]-10α-methoxyergoline | 300 |
| 1,6-Dimethyl-8β-[1',3',5'-trimethyl-2'-pyrroyl-oxyethyl]-10α-methoxyergoline | 100 |
| 1,6-Dimethyl-8β-[1'-ethyl-2'-pyrroyloxyethyl]-10α-methoxyergoline | 180 |
| Nicergoline | 632 |
| Dihydroergotamine | — |

The high value of the therapeutic index of the new compounds in comparison to that of the known prior art compounds clearly appears.

The following examples further illustrate the invention but without limiting it:

EXAMPLE 1

1,6-Dimethyl-8β-cyanomethyl-10α-methoxyergoline (355/649)

15.35 Grams of 1,6-dimethyl-8β-chloromethyl-10α-methoxyergoline are reacted with 3.25 g of potassium cyanide in 500 ml of dimethylsulphoxide at 120° C for 6 hours.

The whole is concentrated under vacuum, then diluted with water. It is filtered off and the residue, dissolved in chloroform, is washed with water and finally concentrated under vacuum.

The residual oil is taken up with ethyl ether and crystallised. 13.9 g are obtained, m.p. 152°–153° C.

EXAMPLE 2

1,6-Dimethyl-10α-methoxy-8β-ergolinyl-acetic acid methyl ester (355/650)

13.9 Grams of 1,6-dimethyl-8β-cyanomethyl-10α-methoxyergoline are refluxed for 5 hours with 27.8 g of potassium hydroxide, 140 ml of dioxane, 75 ml of ethyl alcohol and 90 ml of water.

A further 220 ml of water are added and the mixture is maintained at reflux for 15 hours.

Thereafter it is well dried and the solid is taken up in 400 ml of a solution of 15% sulphuric acid in methanol. The reaction mixture is allowed to stand at room temperature for 24 hours, then poured cautiously over 2 kilos of ice.

The whole is made alkaline with ammonia, concentrated to pH 9, extracted with chloroform and after dryness, the solvent is evaporated under vacuum. The ester appears as a colorless oil (14.17 g) which is characterized as the oxalate, m.p. 152°–153° C.

EXAMPLE 3

1,6-Dimethyl-8β-hydroxyethyl-10α-methoxyergoline (355/666)

To 26.4 g of lithium and aluminum hydride, suspended over 500 ml of anhydrous tetrahydrofuran, are added 13.17 g of methyl ester of 1,6-dimethyl-10α-methoxy-8β-ergolinyl acetic acid, dissolved in 200 ml of anhydrous tetrahydrofuran, while maintaining the temperature at about 60° C.

Thereafter the mixture is reacted always at 60° C for another hour, then at 0° C are added 200 ml of tetrahydrofuran mixed with 100 ml of water.

The whole is filtered off and the filtrate is concentrated under vacuum. The white residue is taken up with acetone and filtered. 10.9 g of 1,6-dimethyl-8β-hydroxyethyl-10α-methoxyergoline are thus obtained, m.p. 235°–236° C.

EXAMPLE 4

1,6-Dimethyl-8β-chloroethyl-10α-methoxyergoline (355/671)

A solution of 10.9 g of 1,6-dimethyl-8β-hydroxyethyl-10α-methoxyergoline, 16 g of pyridinium chloride and 33 g of p-toluenesulphochloride in 400 ml of anhydrous pyridine, is heated to 45°–48° C for 6 hours, then the solvent is removed under vacuum. The residue, dissolved in 600 ml of chloroform, is washed with 10% sodium carbonate and then with water. The chloroform is then removed under vacuum and the residue is chromatographed over a short column of neutral alumina, eluting with chloroform.

Once the solvent is removed, a white oil is obtained which is treated with a little ethyl ether to crystallize. 9.1 g are obtained, m.p. 107°–109° C.

EXAMPLE 5

1,6-Dimethyl-8β-[3',5'-dimethyl-2'-pyrroyloxyethyl]-10α-methoxyergoline (355/679)

0.9 Grams of 1,6-dimethyl-8β-chloroethyl-10α-methoxyergoline are reacted with 0.42 g of sodium, 3,5-dimethyl-2-pyrrolcarboxylate in 2.5 ml of dimethylsulphoxide for 6 hours at 120° C.

Thereafter the whole is poured into 300 ml of cold water and filtered.

The residue is chromatographed over a column containing 15 g of neutral alumina, eluting with chloroform.

Finally, the compound is crystallized from ethyl ether, thereby obtaining 0.7 g of product, m.p. 152°–153° C, yield 64%.

EXAMPLE 6

1,6-Dimethyl-8β-[2'-pyrroyloxyethyl]-10α-methoxyergoline (355/676)

Operating as in Example 5, but employing sodium 2-pyrrolcarboxylate, 1,6-dimethyl-8β-[2'-pyrroyloxyethyl]-10α-methoxyergoline is obtained, m.p. 148°–149° C, yield 60%.

EXAMPLE 7

1,6-Dimethyl-8β-[2'-methyl-3'-pyrroyloxy-ethyl]-10α-methoxyergoline (355/718)

Operating as in Example 5, but employing sodium 2-methyl-3-pyrrolcarboxylate, 1,6-dimethyl-8β-[2'-methyl-3'-pyrroyloxyethyl]-10α-methoxyergoline is obtained, m.p. 213°–215° C, yield 67%.

EXAMPLE 8

1,6-Dimethyl-8β-[1',3',5'-trimethyl-2'-pyrroyloxyethyl]-10α-methoxyergoline (355/717)

Operating as in Example 5, but employing sodium 1,3,5-trimethyl-2-pyrrolcarboxylate, there is obtained 1,6-dimethyl-8β-[1',3',5'-trimethyl-2'-pyrroyloxyethyl]-10α-methoxyergoline (amorphous, oxalate, m.p. 128°–130° C, yield 76%).

EXAMPLE 9

1,6-Dimethyl-8β-[3'-pyrroyloxyethyl]-10α-methoxyergoline (355/740)

Operating as in Example 5, but employing sodium 3-pyrrolcarboxylate, there is obtained 1,6-dimethyl-8β-[3'-pyrroyloxyethyl]-10α-methoxyergoline, m.p. 228°–230° C, yield 78%.

EXAMPLE 10

1,6-Dimethyl-8β-[1'-ethyl-2'-pyrroyloxyethyl]-10α-methoxyergoline (355/741)

Operating as in Example 5, but employing sodium 1-ethyl-2-pyrrolcarboxylate, there is obtained 1,6-dimethyl-8β-[1'-ethyl-2'-pyrroyloxyethyl]-10α-methoxyergoline (amorphous, tartrate, m.p. 96°–98° C, yield 81%).

EXAMPLE 11

1,6-Dimethyl-8β-[5'-bromonicotinoyloxyethyl]-10α-methoxyergoline (355/671)

Operating as in Example 5, but employing the sodium salt of 5-bromonicotinic acid, there is obtained 1,6-dimethyl-8β-[5'-bromonicotinoyloxyethyl]-10α-methoxyergoline, m.p. 187°–190° C.

What is claimed is:

1. An ergoline compound of the formula:

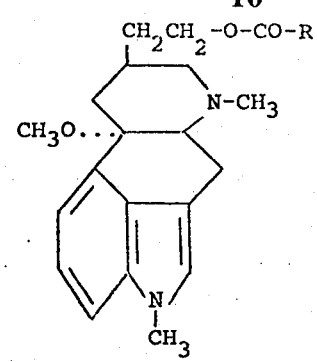

VII wherein R is a pyrrole radical of the formula:

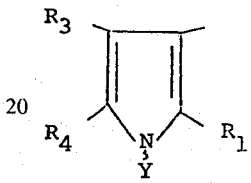 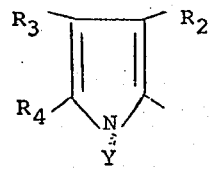

wherein
Y is hydrogen or a lower alkyl radical having from 1 to 4 carbon atoms;
$R_1$ is hydrogen or methyl;
$R_2$ is hydrogen or methyl; and
$R_3$ and $R_4$ are the same or different and are hydrogen, or a lower alkyl radical having from 1 to 4 carbon atoms.

2. 1,6-Dimethyl-8β-[2'-pyrroyloxyethyl]-10α-methoxyergoline.

3. 1,6-Dimethyl-8β-[2'-methyl-3'-pyrroyloxyethyl]-10α-methoxyergoline.

4. 1,6-Dimethyl-8β-[3',5'-dimethyl-2'-pyrroyloxyethyl]-10α-methoxyergoline.

5. 1,6-Dimethyl-8β-[1',3',5'-trimethyl-2'-pyrroyloxyethyl]-10α-methoxyergoline.

6. 1,6-Dimethyl-8β[1'-ethyl-2'-pyrroyloxyethyl]-10α-methoxyergoline.

* * * * *